United States Patent
Pryor et al.

(10) Patent No.: US 9,839,742 B2
(45) Date of Patent: Dec. 12, 2017

(54) BED TRANSPORTABLE MEDICAL STAND MOUNT

(71) Applicant: Pryor Products, Inc., Oceanside, CA (US)

(72) Inventors: Paul Edward Pryor, Fallbrook, CA (US); James Mark Cox, Winchester, CA (US); Richard Enoch Quintania, Fallbrook, CA (US)

(73) Assignee: Pryor Products, Inc., Oceanside, CA (US)

( * ) Notice: Subject to any disclaimer, the term of this patent is extended or adjusted under 35 U.S.C. 154(b) by 0 days.

(21) Appl. No.: 14/712,889

(22) Filed: May 14, 2015

(65) Prior Publication Data

US 2016/0022900 A1   Jan. 28, 2016

Related U.S. Application Data

(60) Provisional application No. 61/994,676, filed on May 16, 2014.

(51) Int. Cl.
*A61M 5/14*       (2006.01)
*F16M 13/02*      (2006.01)

(52) U.S. Cl.
CPC ........ *A61M 5/1415* (2013.01); *A61M 5/1414* (2013.01); *F16M 13/02* (2013.01)

(58) Field of Classification Search
CPC .............. A61M 5/1415; A61M 5/1413; A61M 5/1414; A61M 5/1417; F16M 11/42; F16M 13/02

USPC .......... 248/218.4, 158, 125.8, 511, 518, 519, 248/534, 415, 418, 131, 285.1, 297.21; 280/304.1

See application file for complete search history.

(56) References Cited

U.S. PATENT DOCUMENTS

| | | | | |
|---|---|---|---|---|
| 755,668 | A * | 3/1904 | Hurxthal | B60R 1/078 108/6 |
| 4,511,157 | A | 4/1985 | Wilt, Jr. | |
| 4,511,158 | A * | 4/1985 | Varga | A61G 7/05 248/229.11 |
| 4,572,536 | A * | 2/1986 | Doughty | A61G 5/10 280/304.1 |
| 4,767,131 | A * | 8/1988 | Springer | A61G 5/10 248/316.2 |
| 4,886,237 | A * | 12/1989 | Dennis | A61G 7/05 248/289.11 |
| 4,945,592 | A * | 8/1990 | Sims | A61G 7/05 248/129 |
| 4,966,340 | A | 10/1990 | Hunter | |
| 5,344,169 | A * | 9/1994 | Pryor | A61G 7/0503 248/129 |
| 5,355,539 | A * | 10/1994 | Boettger | A61G 5/10 24/265 C |
| 5,588,166 | A | 12/1996 | Burnett | |
| 5,699,988 | A * | 12/1997 | Boettger | A61G 5/10 248/122.1 |

(Continued)

*Primary Examiner* — Nkeisha Smith
(74) *Attorney, Agent, or Firm* — Gordon Rees Scully Mansukhani, LLP

(57) ABSTRACT

The stand is attached to a wheeled frame by a cylindrical post received in a frame receiver attached to the frame and a rectangular beam is received in a tapered slot in the receiver and extends horizontally from the cylindrical post. The beam terminates at the end opposite the frame receiver in a vertical post.

13 Claims, 2 Drawing Sheets

(56) References Cited

U.S. PATENT DOCUMENTS

| | | | | |
|---|---|---|---|---|
| 5,890,687 | A | 4/1999 | Pryor | |
| 7,497,407 | B2 * | 3/2009 | Blankenship | A61G 7/0503 248/129 |
| 7,748,672 | B2 * | 7/2010 | Walke | A61G 12/002 248/207 |
| 7,845,601 | B1 * | 12/2010 | Culpepper | A61G 7/05 248/125.2 |
| 8,100,371 | B2 * | 1/2012 | Eggleston | A61G 12/008 248/125.8 |
| 8,104,729 | B2 * | 1/2012 | Walke | A61G 12/002 248/125.1 |
| 8,459,602 | B2 * | 6/2013 | Herskovic | A61G 7/0503 248/229.13 |
| 2007/0187559 | A1 * | 8/2007 | Newkirk | A61G 12/005 248/125.8 |
| 2015/0115119 | A1 * | 4/2015 | Hart | A47K 17/022 248/274.1 |
| 2015/0216606 | A1 * | 8/2015 | Bally | F16M 13/022 248/636 |
| 2015/0308615 | A1 * | 10/2015 | Neaves | A01K 1/035 119/61.57 |
| 2016/0000995 | A1 * | 1/2016 | Blankenship | A61M 5/1415 248/514 |

\* cited by examiner

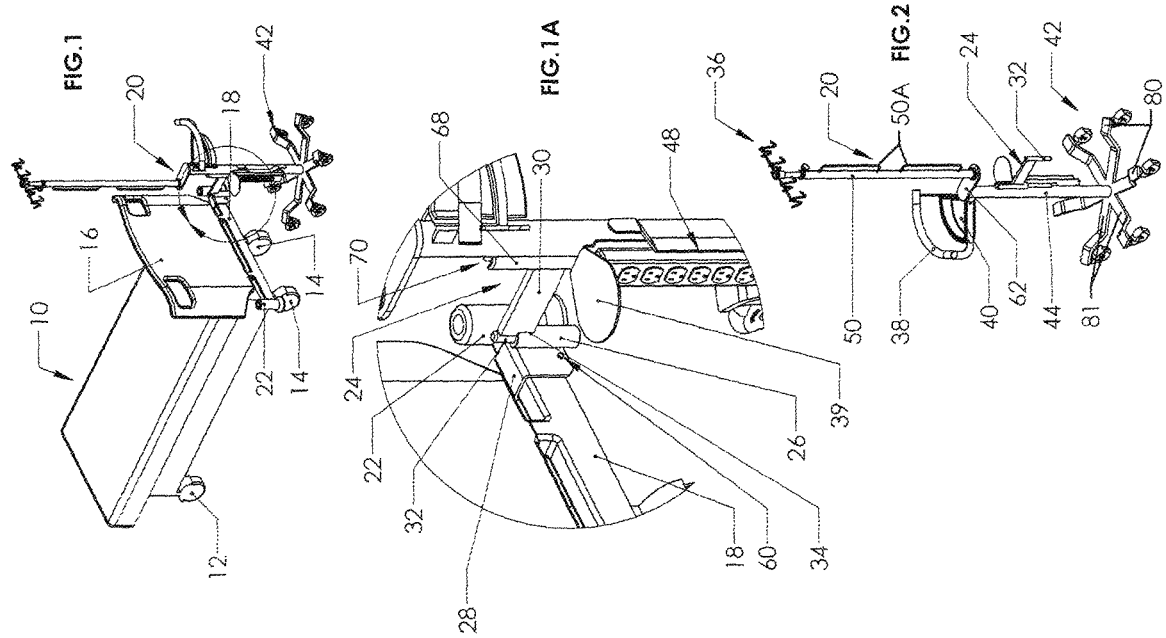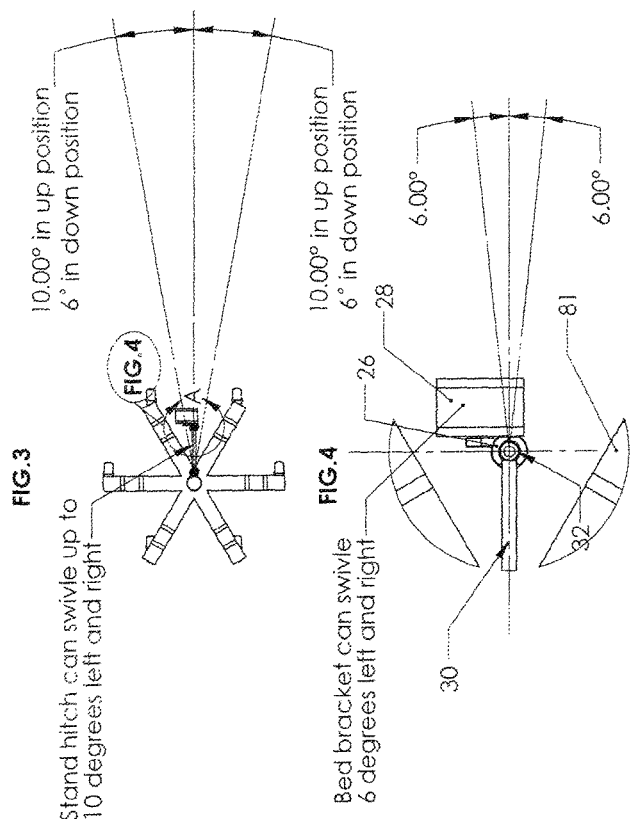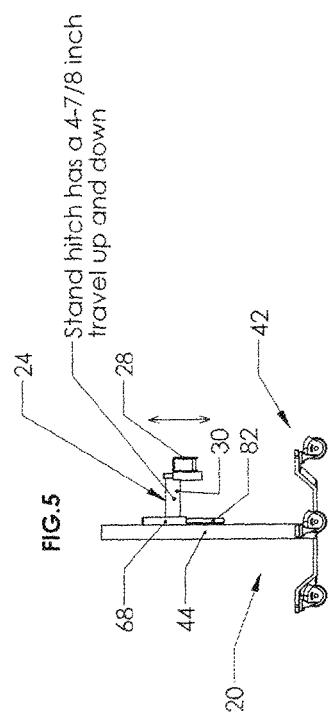

BED TRANSPORTABLE MEDICAL STAND MOUNT

RELATED APPLICATIONS

This application claims priority to a provisional application filed May 16, 2014 and carring application No. 61/994,676.

BACKGROUND OF THE DISCLOSURE

Modern medication dispensing systems such as IV pumps are typically located at a patient's bedside. When it becomes necessary to move the patient, this is frequently accomplished by wheeling the bed and patient from room to room using the wheels commonly provided on hospital beds. However, if the patient is connected to one or more IV pumps, on an IV stand, it is often not possible to move the patient without interrupting the supply of medication, even if two persons are provided (one for the bed and the other for the stand). This is because, in part, the patient is put at risk if the stand is not moved in careful synchronism with the bed. If the stand is allowed to lag behind the bed, the connections to the patient may be broken and the delivery of critical medications interrupted. Therefore it is desirable to mount the stand so that it is connected to the bed. Although it is possible in theory to clamp the stand fixedly to the bed and raise the stand so that it is out of contact with the floor, such an arrangement requires the elevation of a stand that may carry multiple IV pumps or other medical equipment, such as ventilators, that collectively are too heavy to be lifted by one person and which would raise the center of gravity of the bed to the point that it may become unstable particularly on sloped surfaces.

If a wheeled stand is connected to the bed through a hinged connection, with the hinge having a vertical axis, the stand might be trailered behind the bed but the floor surface would have to be perfectly level to avoid binding as the bed travels across irregular surfaces. Since irregular and sloped surfaces are common in medical facilities, especially between connected buildings a simple hinge will not suffice in a majority of circumstances that require moving the bed, patient and medical equipment together.

SUMMARY OF THE INVENTION

The deficiencies in present day solutions in coordinated movement of patients in their hospital bed and with the medical equipment that must remain at their bedside is resolved in an equipment hitch that is attached to a bed rail (typically at the front or rear of the bed) and the other end to a medical stand. The connection to the medical stand allows a selected degree of freedom of movement to allow for variations in floor height and slope and allow turns to be initiated. In an exemplary embodiment the swiveling is in the attachment to the medical stand. The hitch also accommodates a difference in floor level by allowing limited vertical movement of the stand relative to the bed.

The stand hitch accommodates a vertical pin in a cylindrical receiver on the bed. The cylindrical receiver has a slot that receives a rectangular beam that extends from the stand. The beam has a vertical pin that is received in a cylindrical, vertically-oriented, pin receiver on the stand. The slot in the pin receiver is sized to securely hold the beam from swiveling. The hitch is attached to the bed by a bed bracket which can accommodate bed rails of different beds. The bracket is secured to the bed rail without the necessity of modifying the bed rail, so that the structural integrity and surface finish of the bed rail are not compromised.

The stand is connected to the hitch by a vertical pin which fits within a vertical slot in a part cylindrical stand pin receiver. The slot is large enough to permit limited pivoting of the pin and associated beam. At the same time the beam and pin can move vertically a sufficient difference for the bed to be pushed, for example, over a raised threshold that causes the bed to temporally be higher than the trailing stand.

BRIEF DESCRIPTION OF THE DRAWINGS

FIG. 1 shows a patient bed with a medical stand attached to the bed rail and in position for transport FIG. 1A is an enlargement of circled area in FIG. 1 showing the bed bracket and pin receiver attached to the a bed rail and the rectangular beam extending to and engaging the stand.

FIG. 2 shows the wheeled medical stand with the hitch beam attached to the stand and with the vertical pin positioned for engagement with pin receiver on the bed rail.

FIG. 3 is a top view of the stand base showing the position of the hitch beam supporting the bed bracket.

FIG. 4 is an enlargement of the circled area on FIG. 3 showing the bed bracket.

FIG. 5 is a side view of the lower portion of the medical stand showing the part-cylindrical receiver that receives a pin on the beam connecting the medical stand and bed.

DETAILED DESCRIPTION OF THE DRAWINGS

Figure 6:
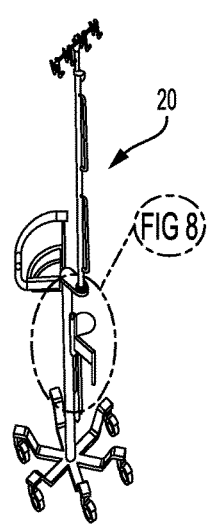
FIG. 6 is a prospective view of the stand showing the same structure as FIG. 2, but market to indicate the enlarged view of FIG. 8.

Referring to FIG. 1 the bed 10 has wheels on the forward part of the bed (a single wheel is visible in the Figure). The rear of the bed is supported on two castering wheels 14 and a head board 16. The medical stand 20 is shown in trailering position off center of the bed to allow access for an attendant to access the headboard 16. This is accomplished by the stand being mounted close to the wheel mount 20 for the bed 10. This configuration makes it possible for an attendant to access to the head board to push the bed. A bed rail 18 extends between the two castering wheels 14 and their mounts 22.

Referring to FIG. 1A the bed bracket 28 is fitted over the bed rail 18. Vertical movement of the bracket 28 is prevented by the use of a bolt or pin (not shown) received in the opening 60. The bracket 28 also mounts a pin receiver 26 to receive the hitch pin 32. Pin 32 is mounted on the beam 30. The rectangular beam 30 mounts a second pin (See pin 82 in FIG. 5). The slot 34 serves to limit the vertical travel of pin 32 and to keep the beam in alignment with the bed. It has been found that the pivoting movement does not limit the turning radius of the bed because the wheeled base 42 can accommodate a tight turn once the turn is initiated and after the beam hits the sides of slot 34.

Also illustrated in FIG. 1A is the power strip 48 mounted on the lower portion of pole 44. Guard 39 protects against inadvertent unplugging of any equipment plugged into the power strip because it acts as a "stand off" structure so that, for example, attendants will be prevented from too closely approaching the power strip. In addition the guard protects the outlets from any spilled fluids.

In FIG. 1A illustrates the details of the hitch 24. The hitch 24 comprises a rectangular beam 30 with a vertical hitch pin 32 received in a cylindrical receiver 26 attached to the bed bracket 28. The rectangular beam is constrained to limited vertical movement by the pin 32 being received in the cylindrical mount 26 and to swiveling movement by engagement of beam with slot 34. In the exemplary embodiment the slot 34 is larger than the width of the beam 30 a sufficient extent to permit limited swiveling. The slot is tapered so that approximately 6 degrees of swiveling on either side of center when the pin is fully inserted and approximately 10 degrees of swiveling on either side of center when the pin is near its upper limit of vertical travel in the slot.

It has been found that the limits on pivoting are sufficient to prevent "scrubbing" of the wheels on the base 42. For tighter radius turns the castering wheels on the stand merely pivot whatever degree is necessary to accommodate the tighter turn (the casters have 360 degree freedom of pivoting).

FIG. 2 shows the stand 20 unattached to a bed. A base post 44 extends upwards from the wheeled base 42 which is supported by multiple castered wheels 80 at the outer ends of the arms 81. The pole 44 to supports the entire upper structure of the stand including a part circular push handle 38. The push handle is attached to the base post by integral extensions of the push handle 38. In the illustrated embodiment the push handle creates a triangular space with may be filed by a tray 40. An offset beam 62 extends from the base post 44 and mounts an upper pole 50. The upper pole 50 is offset so that equipment, such as IV pumps that are mounted on the upper pole 50 do not significantly alter the position of the center of gravity from being centered on the wheeled base 42. The upper pole 50 supports a hook top 36 from which multiple IV bags can be hung to supply fluids to the patient directly, or in the usual case, supply IV pumps (not shown) that are supported on the stand 20. Ribs 50A prevent inadvertent and device mounting not over the center of gravity of the base.

FIG. 3 shows the angular extent to which the stand can swivel before the casters take over to accommodate the tightest turns. The area which is detailed in FIG. 4 is shown in the circled caption.

FIG. 4 shows the bed bracket 28 oriented in between two of the base arms 81.

FIG. 5 is a side view of the stand 20, showing the stand pin 82 protruding from the lower end of the channel 68. The hitch 24 includes the beam 30 carrying the bracket 28.

Figure 8:
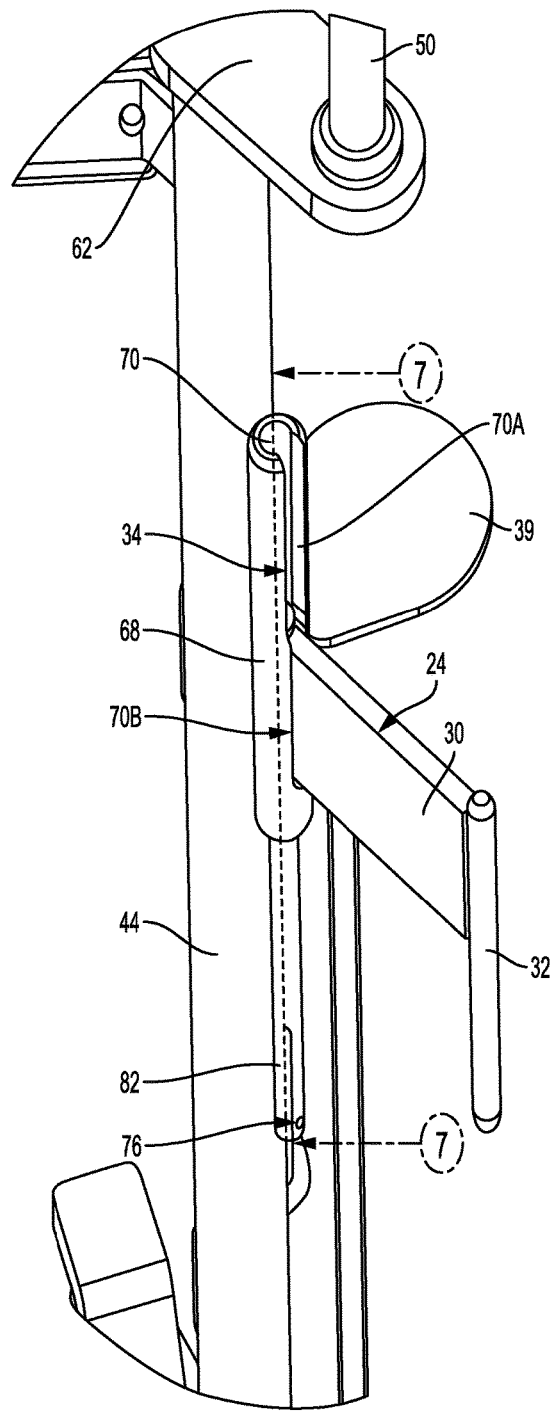
FIG. 8 is a prospective view of the stand showing an enlarged view of the area encircled in FIG. 6.

FIG. 6 is a perspective view showing the same detail as FIG. 2 but indicating the detailed section of the stand 20 that is illustrated in FIG. 8.

FIG. 8 shows the detail of the stand mount which comprises the channel 68 with the slot 34. The slot 34 is shown to have a wider upper section 70A and a narrower lower section 70B. The beam 30 is shown in its lowest position where the beam is stopped by the bottom of slot 70B. In this position the beam is free to rotate on pin 82 through 6 degrees left and right of center. When the beam 30 is in the upper section 70A the wider channel there permits movement left and right of 10 degrees. At the lower end of pin 82, there is a retention bore 76 into which a screw or bolt can be inserted to prevent the pin 82 from being lifted out of the channel 68. The beam supports the pin 32 which can be inserted in the bracket receiver 26 (See FIG. 1A).

Figure 7:
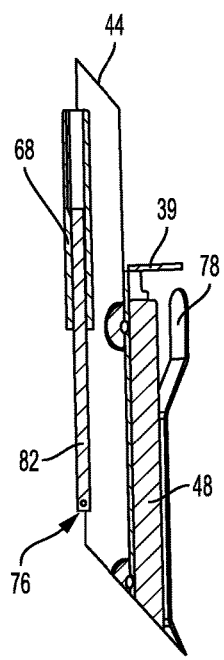
FIG. 7 is a sectional view taken on line 7-7 of FIG. 8 and showing the stand pin in the stand receiver.

FIG. 7 is a sectional view taken on line 7-7 of FIG. 8. The pin 82 and its retention bore 76 are shown. A cord hook 48 is shown which allows the cord for the power strip 48 to be stowed during transport.

In use, the stand 20 is positioned near the bracket 28. The attendant lifts the beam 30 so that the bottom of the pin 32 will clear the top of the receptacle 26 and inserts the pin into the receptacle 26 and lowers the beam until the beam is received in slot 34. The power strip 48 has a cord hook 78 for stowing the power cords when the stand is in transit or idle.

In the usual relationship between bed rail and stand and on a flat floor, the beam will be about one-half of the way down the channel 68 so that the hitch is ready to accommodate vertical displacement of the stand as compared to the bed in either direction (up or down).

With the pin 32 in the receptacle 26 and the pin 82 in the channel 68, the bed is ready for transport. An attendant can push the bed from the head board 16 and the stand 20 will follow the movement of the bed 10 in the manner of a trailer. When a turn is initiated the freedom of rotation of the beam 30 in the slotted channel 68 causes the stand to follow the curved path of the bed until the limits of rotation are reached. During the initial rotation of the beam in the slot 68 the wheels of the castered base 42 have stabilized in alignment with the curved path of the bed. If the attendant tightens the turn the casters will smoothly follow the new curved path by further rotation of the casters because the casters have already been stabilized with the initial turn.

When the bed encounters an uneven surface or an incline (such as a ramp) the pin 82 can ride up and down the slotted channel of receiver 68 which prevents the stand 20 from blocking the bed from negotiating the incline or obstacle.

SUMMARY

The invention provides a way to keep an IV stand in position at the head of the bed even while the bed is being rolled to a new location. A hitch is employed to make the connection between the bed and stand so that they can be transported together without disturbing the delivery of medication to the patient. The hitch has a vertical pin at each end. In the case of the bed end the pin is relatively short and the beam is constrained by a channel in the pin receiver so that a stable connection is achieved. The opposite end of the beam is longer and is fitted into a slotted channel on the base within which the beam can move up and down to accommodate, for example, the stand being lower than the bed (as in going up a ramp). Thereby the stand can accommodate inclined or irregular surfaces by the freedom of the pin to move up and down in the slotted channel. At the same time the slotted channel permits limited angular displacement of the stand relative to the bed and that causes the bed and stand combination to smoothly negotiate turns because before the limit of rotation has been reached. When the casters have aligned themselves to the initial turn a tighter turn radius merely causes coordinated further castering. The device may be attached to a bed rail without having to modify or mar the bed rail. The process of connecting the bed and stand is facilitated by the same vertical travel of the pin and beam but in this case the beam is merely lifted and inserted into the (bed) receiver which prohibits angular movement of the beam at the bed end.

The invention claimed is:

1. A system including a wheeled stand attached to a movable frame comprising:

a pin receiver on the frame that is sized to receive a hitch pin and having a slot adapted to receive a beam, the beam having two spaced ends, wherein one end is attached to the hitch pin and wherein the beam extends horizontally and at a right angle to the frame, the beam being adapted to be attached to the wheeled stand, the beam and hitch pin being free to move vertically in the pin receiver;

wherein a width of the slot is greater than a width of the beam so that the beam can rotate relative to the pin receiver, wherein the rotation of the beam is limited by a difference in width of the slot and width of the beam; and the width of the slot at its upper end is wider than the width of the slot at its lower end.

2. The system according to claim 1, wherein:

a stand post attached to the beam at an end opposite the hitch pin, stand post receiver on the wheeled stand adapted to rotatably receive the stand post.

3. The system according to claim 2, wherein: rotation of the stand post relative to the stand post receiver is limited.

4. The system according to claim 2, wherein: the pin receiver is cylindrical.

5. A mounting system attaching wheeled stand to a movable frame comprising:

a beam extending between the wheeled stand and the frame;

wherein the beam has a first end and a second end, the first end including a stand post that is configured to be connected to a stand post receiver on the wheeled stand;

wherein the stand post receiver includes a slot for receiving the beam;

wherein a width of the slot is greater than a width of the beam so that the beam can rotate relative to the stand post receiver, and wherein the rotation of the beam is limited by a difference in width of the slot and width of the beam; and wherein the width of the slot varies and the width of the slot at its upper end is wider than the width of the slot at its lower end.

6. The mounting system of claim 5, wherein the second end of the beam includes a pin, and wherein the pin is rotatably received within a pin receiver located on the frame.

7. The mounting system of claim 6, wherein the rotation of the pin relative to the pin receiver is limited.

8. The mounting system of claim 6, wherein the pin receiver is cylindrical.

9. A system including a wheeled stand for carrying at least one IV pump, wherein the stand is configured to be connected to a wheeled bed frame so that the bed frame and stand move together utilizing the wheels on both the stand and the bed frame, wherein the system comprises:

the wheeled stand including a vertical upper pole and a vertical base post, wherein the upper pole is offset from the base post by an offset beam so that the IV pump mounted on the upper pole does not cause the stand to become unstable by altering the center of gravity of the stand;

a connecting beam extending between the wheeled stand and the frame;

wherein the connecting beam has a first end and a second end, the first end including a stand post that is configured to be connected to a stand post receiver on the wheeled stand;

wherein the stand post receiver includes a slot for receiving the connecting beam;

wherein a width of the slot is greater than a width of the connecting beam so that the connecting beam can rotate relative to the stand post receiver, and wherein the rotation of the connecting beam is limited by a difference in width of the slot and width of the beam.

10. The system of claim 9, wherein the width of the slot varies and the width of the slot at its upper end is wider than the width of the slot at its lower end.

11. The system of claim 9, wherein the second end of the connecting beam includes a pin, and wherein the pin is rotatably received within a pin receiver located on the frame.

12. The system of claim 11, wherein the rotation of the pin relative to the pin receiver is limited.

13. The system of claim 11, wherein the pin receiver is cylindrical.

* * * * *